United States Patent [19]
Löbberding et al.

[11] Patent Number: 5,623,049
[45] Date of Patent: Apr. 22, 1997

[54] NUCLEIC ACID-BINDING OLIGOMERS POSSESSING N-BRANCHING FOR THERAPY AND DIAGNOSTICS

[75] Inventors: Antonius Löbberding, Wuppertal; Burkhard Mielke, Leverkusen; Christoph Schwemler, Leichlingen; Eckhard Schwenner, Wuppertal; Udo Stropp, Haan; Wolfgang Springer, Wuppertal; Axel Kretschmer, Bergisch Gladbach; Thorsten Pötter, Köln, all of Germany

[73] Assignee: Bayer Aktiengesellschaft, Leverkusen, Germany

[21] Appl. No.: 300,884

[22] Filed: Sep. 6, 1994

[30] Foreign Application Priority Data

Sep. 13, 1993 [DE] Germany .................. 43 31 012.5

[51] Int. Cl.$^6$ .............................. C07K 7/00; C07H 5/04; C07H 21/04; C07D 239/00
[52] U.S. Cl. .................. 530/300; 536/24.3; 536/18.7; 536/24.5; 544/242; 544/244; 544/264; 562/575
[58] Field of Search ................ 514/44, 2; 536/24.5, 536/24.3, 24.31, 24.32, 18.7; 530/300; 562/575; 544/242, 244, 264

[56] References Cited

FOREIGN PATENT DOCUMENTS

| | | | |
|---|---|---|---|
| 0300796 | 1/1989 | European Pat. Off. .......... | C12Q 1/68 |
| WO8605518 | 9/1986 | WIPO .................. | C12Q 1/68 |
| WO9218518 | 10/1992 | WIPO .................. | C07H 19/048 |
| WO9220702 | 11/1992 | WIPO .................. | C07K 5/00 |
| WO9220703 | 11/1992 | WIPO .................. | C07K 5/00 |
| WO9304701 | 3/1993 | WIPO .................. | A61K 48/00 |

OTHER PUBLICATIONS

B. Hyrup et al., J. Am. Chem. Soc. 116 ('94) 7964–70.
H. Kang et al., Biopolymers ('92) 32(10) 1351–63 Abstract.
R. McGraw et al., BioTechniques, 8(6) ('90) 674–8.
F. Flan, Science, vol. 262 (Dec. 10, 1993) 1647–49.
E. Uhlmann et al., Chemical Rev., 90(4) ('90) 543–584.
C. Stein et al., Science, 261 (Aug. 20, 1993) 1004–1012.
J. Milligan et al., J. Med. Chem. ('93) 36(14) 1923–37.
P. Nielsen et al., Science, 254 (Dec. 6, 1991) 1497–1500.
C. Helene et al., B. B. Aora 1049 ('90) 99–125.
Chemical Abstracts, vol. 94, Feb. 2, 1981, No. 5, pp. 1/185; CA# 26354j: "Specific interaction between oligovaline...", S.A. Strel'tsov et al.

Chemical Abstracts, vol. 113, Nov. 19, 1990, No. 21; pp. 1/776; CA# 191856t: "Preparation of oligodeoxyribonucleotide...", P. Westermann et al.
Elsevier Science Publishers LTD, Tibtech, May 1992, vol. 10, pp. 152–158; "Antisense oligonucleotides as antiviral agents", S. Agrawal.
Antiviral Chemistry & Chemotherapy, vol. 2, No. 4, 1991, pp. 191–214; "Towards gene–inhibition therapy: a review of progress...", W. James.
Cancer Research, vol. 51, Sep. 1, 1991, pp. 4505–4510; "Inhibition of Protooncogene expression by antisense oligodeoxynucleotides...", B. Calabretta.
Anti-Cancer Drug Design, 1991, vol. 6, pp. 569–584; "The anti-gene strategy: control of gene expression by triplex–...", C. Hélène.
Chemical Reviews, American Chemical Society, Jun. 1990, vol. 90, No. 4, pp. 544–584/cover page; "Antisense Oligonucleotides: a new...", E. Uhlmann et al.
The Journal of Organic Chemistry, vol. 33, No. 4, Apr. 1968, pp. 1341–1344; "N–vinyl derivatives of substituted pyrimidines...", J. Pitha et al.
Advances in polymer Science 50, Springer–Verlag Berlin Heidelberg, 1983, pp. 1–16; "Physiological activities of synthetic analogs...", J. Pitha.
Tetrahedron Letters, vol. 32, No. 50, pp. 7385–7388, 1991; "Solid phase synthesis of neutral oligonucleotide analogues", H. Wang et al.
Tetrahedron Letters, vol. 34, No. 8, pp. 1275–1278, 1993; "Peptide-based nucleic acid surrogates incorporating...", P. Garner et al.
J. Org. Chem., 1991, vol. 56, pp. 6007–6018; "Acyclic nucleic acid analogues: synthesis and oligomerization of...", S.B. Huang et al.

Primary Examiner—Charles C.P. Rories
Attorney, Agent, or Firm—Sprung Horn Kramer & Woods

[57] ABSTRACT

The invention relates to nucleic acid-binding oligomers possessing N-branching of the general formula (I),

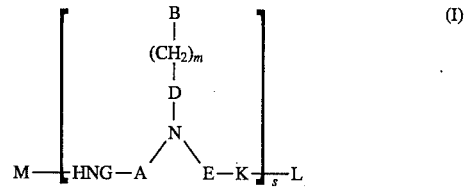

and their monomers, where the individual radicals have the meaning given in the description, and to their use as medicaments or as aids in diagnostics.

16 Claims, No Drawings

NUCLEIC ACID-BINDING OLIGOMERS POSSESSING N-BRANCHING FOR THERAPY AND DIAGNOSTICS

BACKGROUND OF THE INVENTION

The specific switching-off of gene expression by complementary nucleic acids, so-called antisense oligonucleotides, represents a-novel therapeutic approach. Possible applications-extend from the treatment of vital infections through to the therapy of cancer (S. Agrawal, Tibtech 10, 152 (1992); W. James, Antiviral Chemistry & Chemotherapie 2, 191 (1991); B. Calabretta, Cancer Research 51, 4504 (1991)). The control of gene expression is effected at the level of DNA and RNA and is achieved even with unmodified oligonucleotides (C. Helene, Anti-Cancer Drug Design 6, 569 (1991); E. Uhlmann, A. Peymann, Chemical Reviews 90, 543 (1990)). However, owing to insufficient stability towards enzymes and inadequate uptake into cellular systems, these oligonucleotides are not suitable for therapeutic applications. Therapeutic applications require chemically modified antisense oligonucleotides.

Oligonucleotides possessing a modified internucleotide phosphate or a phosphate-free internucleotide linkage have been systematically investigated in many studies; however, their synthesis has proved to be very elaborate and observed therapeutic effects to be unsatisfactory (E. Uhlmann, A. Peymann, Chemical Reviews 90, 543 (1990)).

One alternative to modifying or substituting the phosphate group in nucleic acids is completely to replace ribose and phosphate by other backbones. This concept was realized for the first time by Pitha et al., who replaced ribose phosphate by poly-N-vinyl derivatives, leading to so-called "plastic DNA" (J. Pitha, P.O.P. Ts'O, J. Org. Chem. 33, 1341 (1968); J. Pitha, J. Adv. Polym. Sci. 50, 1 (1983)). However, this does not permit the specific construction of defined sequences.

The synthesis of defined sequences is achieved if, for example, a polyamide backbone, which is built up step-wise in analogy with conventional peptide synthesis (M. Bodanszky, Principles of Peptide Synthesis, Springer, Berlin 1984), is used in place of sugar phosphate. This concept has been realized in differing ways by a variety of research groups (J. E. Summerton et al. WO 86/05518; R. S. Varma et al. WO 92/18518; O. Buchardt et al. WO 92/20702; H. Wang, D. D. Weller, Tetrahedron Letters 32, 7385 (1991); P. Garner, J. U. Yoo, Tetrahedron Letters 34, 1275 (1993); S.-B. Huang, J. S. Nelson, D. D. Weller; J. Org. Chem. 56, 6007 (1991)).

Polyamide nucleic acids are likewise suitable for diagnostic and molecular-biological applications (Buchardt et al. WO 92/20703).

SUMMARY OF THE INVENTION

During the course of work with structures of this type, the synthesis of novel N-branched oligomeric nucleic acids was successfully achieved. These nucleic acids were found to bind surprisingly well to DNA and RNA. The substances are suitable for controlling gene expression, and exhibit antiviral properties. Furthermore, substances of this type can be used in diagnostics and molecular biology for isolating, identifying and quantifying nucleic acids.

The structures described below were synthesized:

The invention relates to compounds of the general formula (I),

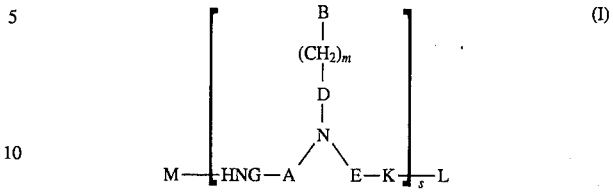

in which

A represents $-(CH_2)_n-$ or $-CO-$,

B represents all natural or unnatural nucleobases, such as, for example, thymine, uracil, cytosine, adenine, guanine or hypoxanthine, or derivatives derived therefrom by chemical modification, or halogenated precursors thereof, optionally substituted on the amino groups by protective groups such as acetyl, trifluoroacetyl, trichloroacetyl, benzoyl, phenylacetyl, benzyloxycarbonyl, tert-butyloxycarbonyl, allyloxycarbonyl or (9-fluorenyl)methoxycarbonyl, or other protective groups which are customary in peptide and nucleic acid chemistry, or possessing free amino groups, D represents $-(CO)_p-$, E and G, independently of each other, represent $-CHR-$, where R represents H or a residue of a natural or unnatural amino acid, e.g. from glycine, alanins, valine, leucine, isoleucine, serine, threonine, cystsine, methionine, phenylalanine, tyrosine, histidine, tryptophan, lysine, ornithine, asparagine, aspartic acid, glutamine, glutamic acid, arginine, proline, hydroxyproline or sarcosine, dehydroamino acids, such as, for example, dehydroalanine or dehydro-α-aminobutyric acid, other unnatural amino acids, such as phenylglycine, 4-nitrophenylalanine, 3-nitrophenylalanine, 2-nitrophenylalanine, 2-, 3- or 4-aminophenylalanine, 3,4-dichlorophenylalanine, 4-iodophenylalanine, 4-methoxyphenylalanine, 1-triazolylalanine, 2 -pyridylalanine, 3-pyridylalanine, 4-pyridylalanine, 1-naphthylalanine or 2-naphthylalanine, optionally possessing protective groups, in their D or L form, or, optionally, E and G are linked together via an alkyl chain $-(CH_2)_q-$, K represents $-CO-$, $-SO_2-$ or $-CH_2-$, L can be a carrier system, reporter ligand, a solubility-mediating group or hydrogen, M can, independently of L, be a carrier system, reporter ligand, a solubility-mediating group or hydrogen, m can be 0, 1, 2 or 3, n can be 0, 1, 2, 3 or 4, p can be 0, 1 or 2, q can be 0, 1 or 2, and s can assume values of between 1 and 30.

Compounds of the general formula (I) are preferred in which

A represents $-(CH_2)_n-$ or $-CO-$,

B represents all natural nucleobases, such as, for example, thymine, uracil, cytosine, adenine, guanine or hypoxanthine, or halogenated precursors thereof, optionally substituted on the amino groups by protective groups such as acetyl, trifluoroacetyl, trichloroacetyl, benzoyl, phenylacetyl, benzyloxycarbonyl, tert-butyloxycarbonyl, allyloxycarbonyl or (9-fluorenyl)methoxycarbonyl, or other protective groups which are customary in peptide and nucleic acid chemistry, or possessing free amino groups, D represents $-(CO)_p-$, E and G, independently of each other, represent $-CHR-$, where R represents H or a residue of a natural or unnatural amino acid, e.g. from glycine, alanins, valine, leucine, isoleucine, serine, threonine, cystsine, methionine, phenylalanine, tyrosine, histidine, tryptophan, lysine, ornithine, asparagine, aspartic acid, glutmine, glutamic acid, arginine, proline, hydroxyproline or sarcosine, dehydroamino acids, such as, for example, dehydroalanine or dehydro-α-aminobutyric acid, other unnatural amino acids, such as phenylglycine, 2-pyridylalanine, 3-pyridylalanine, 4-pyridylalanine, 1-naphthylalanine or 2-naphthylalanine, optionally possessing protective groups, in their D or L form, or, optionally, E and G are linked together via an alkyl chain $-(CH_2)_q-$, K can be $-CO-$, $-SO_2-$ or $-CH_2-$, L can be a carrier system, reporter ligand, a solubility-mediating group or hydrogen, M can, independently of L, be a carrier system, reporter ligand, a solubility-mediating group or hydrogen, m can be 0, 1, 2 or 3, n can be 0, 1, 2 or 3, p can be 0 or 1, q can be 0, 1 or 2, and s can assume values of between 3 and 20.

The invention relates furthermore to compounds of the general formula (II),

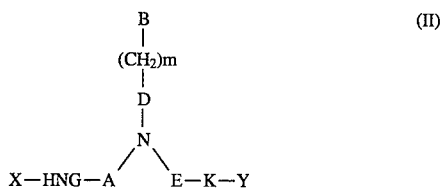

(II)

in which

A represents $-(CH_2)_n-$ or $-CO-$,

B represents all natural or unnatural nucleobases, such as, for example, thymine, uracil, cytosine, adenine, guanine or hypoxanthine, or derivatives derived therefrom by chemical modification, or halogenated precursors thereof, optionally substituted on the amino groups by protective groups such as acetyl, trifluoroacetyl, trichloroacetyl, benzoyl, phenylacetyl, benzyloxycarbonyl, tert-butyloxycarbonyl, allyloxycarbonyl or (9-fluorenyl)methoxycarbonyl, or other protective groups which are customary in peptide and nucleic acid chemistry, or possessing free amino groups, D represents $-(CO)_p-$, E and G, independently of each other, represent $-CHR-$, R represents H or a residue of a natural or unnatural amino acid, e.g. from glycine, alanine, valine, leucine, isoleucine, serine, threonine, cysteine, methionine, phenylalanine, tyrosine, histidine, tryptophan, lysine, ornithine, asparagine, aspartic acid, glutamine, glutamic acid, arginine, proline, hydroxyproline or sarcosine, dehydroamino acids, such as, for example, dehydroalanine or dehydro-α-aminobutyric acid, other unnatural amino acids, such as phenylglycine, 4-nitrophenylalanine, 3-nitrophenylalanine, 2-nitrophenylalanine, 2-, 3- or 4-aminophenylalanine, 3,4-dichlorophenylalanine, 4-iodophenylalanine, 4-methoxyphenylalanine, 1-triazolylalanine, 2-pyridylalanine, 3-pyridylalanine, 4-pyridylalanine, 1-naphthylalanine or 2-naphthylalanine, optionally possessing protective groups, in their D or L form, or, optionally, E and G are linked together via an alkyl chain $-(CH_2)_q-$, K represents $-CO-$, $-SO_2-$ or $-CH_2-$, X represents an arbitrary protective group known from peptide chemistry, H, or an arbitrary natural or unnatural amino acid in protected or unprotected form, Y represents COOH, CSOH, $CH_2OH$, COOR", with R" being an arbitrary protective group from peptide chemistry, carrier, reporter ligand or solubility-mediating group, and n can be 0, 1, 2, 3 or 4, and q can be 0, 1 or 2.

Compounds of the general formula (II) are preferred in which

A represents $-(CH_2)_n-$ or $-CO-$,

B represents all natural nucleobases, such as, for example, thymine, uracil, cytosine, adenine, guanine or hypoxanthine, or halogenated precursors thereof, optionally substituted on the amino groups by protective groups such as acetyl, trifluoroacetyl, trichloroacetyl, benzoyl, phenylacetyl, benzyloxycarbonyl, tert-butyloxycarbonyl, allyloxycarbonyl or (9-fluorenyl) methoxycarbonyl, or other protective groups which are customary in peptide and nucleic acid chemistry, or possessing free amino groups, D represents $-(CO)_p-$, E and G, independently of each other, represent $-CHR-$, R represents H or a residue of a natural or unnatural amino acid, e.g. from glycine, alanine, valine, leucine, isoleucine, serine, threonine, cysteine, methionine, phenylalanine, tyrosine, histidine, tryptophan, lysine, ornithine, asparagine, aspartic acid, glutamine, glutamic acid, arginine, proline, hydroxyproline or sarcosine, dehydroamino acids, such as, for example, dehydroalanine or dehydro-α-aminobutyric acid, other unnatural amino acids, such as phenylglycine, 2-pyridylalanine, 3-pyridylalanine, 4-pyridylalanine, 1-naphthylalanine or 2-naphthylalanine, optionally possessing protective groups, in their D or L form, or, optionally, E and G are linked together via an alkyl chain $-(CH_2)_q-$, K can be $-CO-$, $-SO_2-$ or $-CH_2-$, X represents an arbitrary protective group known from peptide chemistry, H, or an arbitrary natural or unnatural amino acid in protected or unprotected form, Y represents COOH, CSOH, $CH_2OH$, COOR", with R" being an arbitrary protective group from peptide chemistry, carrier, reporter ligand or solubility-mediating group, and n can be 0, 1, 2 or 3, and q can be 0, 1 or 2.

Compounds of the general formula (II) are particularly preferred
in which

A represents —(CH$_2$)$_n$— or —CO—,

B represents all natural nucleobases, such as, for example, thymine, uracil, cytosine, adenine, guanine or hypoxanthine, or halogenated precursors thereof, optionally substituted on the amino groups by protective groups such as acetyl, trifluoroacetyl, trichloroacetyl, benzoyl, phenylacetyl, benzyloxycarbonyl, tert-butyloxycarbonyl, allyloxycarbonyl or (9-fluorenyl)methoxycarbonyl, or other protective groups which are customary in peptide and nucleic acid chemistry, or possessing free amino groups, D represents —(CO)$_p$—, E and G, independently of each other, represent —CHR—, R represents H or a residue of a natural or unnatural amino acid, e.g. from glycine, alanine, valine, leucine, isoleucine, serine, threonine, cysteine, methionine, phenylalanine, tyrosine, histidine, tryptophan, lysine, ornithine, asparagine, aspartic acid, glutamine, glutamic acid, arginine, proline, hydroxyproline or sarcosine, or dehydroamino acids, such as, for example, dehydroalanine or dehydro-α-aminobutyric acid, optionally possessing protective groups, in their D or L form, or, optionally, E and G are linked together via an alkyl chain —(CH$_2$)$_q$—, K is —CO—, X represents an arbitrary protective group known from peptide chemistry, H, or an arbitrary natural or unnatural amino acid in protected or unprotected form, Y represents COOH, CSOH, CH$_2$OH, COOR", with R" being an arbitrary protective group from peptide chemistry, carrier, reporter ligand or solubility-mediating group, and n can be 0, 1, 2 or 3, and q can be 0 or 1.

By carrier system or reporter ligand is meant a cell-specific binding and recognition agent which binds specifically to the cell surface and brings about internalization of the nucleic acid-binding oligomers on which the invention is based. The internalization can be effected in various ways, e.g. by endocytosis or by active transport mechanisms.

The structure of the cell surface can be a protein, polypeptide, carbohydrate or lipid, or a combination thereof. Typically, the uptake into the cell is brought about by surface receptors. For this reason, the binding and recognition agent can be a natural or synthetic ligand of a receptor.

The ligand can be a protein, polypeptide, carbohydrate or lipid, or a combination of these, provided with functional groups which are so arranged that they can be recognized by the cell-surface structure. It can also be a component or the entirety of a biological organism, e.g. of a virus or a cell, or be an artificial transport system, such as, for example, liposomes. It can, furthermore, be an antibody or an analogue of an antibody.

Different ligands must be employed for directing the oligomers to different cells. Suitable ligands for directing the oligomers to macrophages are, preferably, carbohydrates, such as, for example, mannose, polycations, such as, for example, polylysines, polyarginines and polyornithines, basic proteins, such as, for example, avidin, as well as glycopeptides, peptides or lipopeptides (G. Y. Chu et al., WO 92/9304701).

By solubility-mediating groups are meant functional groups which mediate solubility of the oligomers in water. These can, for example, be esters or amides of amino acids, hydroxycarboxylic acids, aminosulphonic acids, hydroxysulphonic acids or diamines. Amides of diaminocarboxylic acids, such as ornithine or lysine, or 2,4-diaminobutyric acid, are preferred.

DESCRIPTION OF THE PREFERRED EMBODIMENTS

Peptide-nucleic acids possessing a glycylglycine backbone

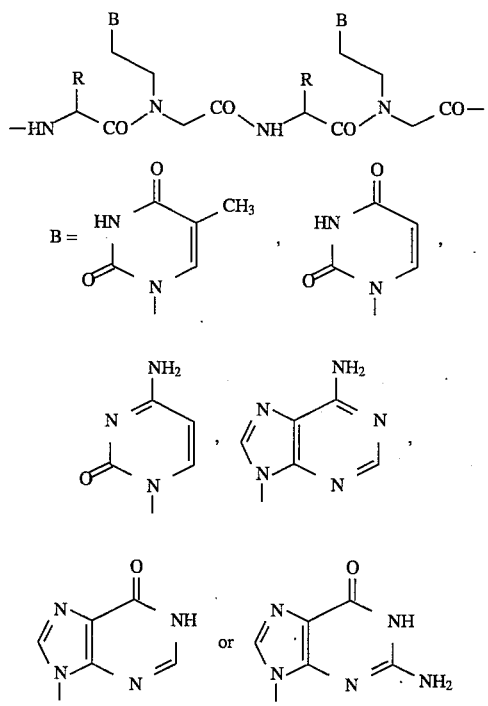

In the case of the compounds of this type, the ribose phosphate backbone or deoxyribose phosphate backbone of RNA or DNA, respectively, is replaced by a polyamide backbone consisting of glycylglycine dipeptides (R=H). The resulting oligomer is notable for a high degree of flexibility. In addition, a multiplicity of further compounds possessing differing properties (e.g. polarity and charge distribution) can be made available by incorporating other amino acids instead of glycine in every second position (R≠H).

Peptide-nucleic acids possessing a 4-aminoproline backbone

In this type of structure, the ribose phosphate backbone or deoxyribose phosphate backbone of the natural nucleic acids is replaced by a polymer based on 4-aminoproline. Compounds of low flexibility result. Depending on the configuration which is present on each occasion, different pre-orientations of the oligomers are achieved.

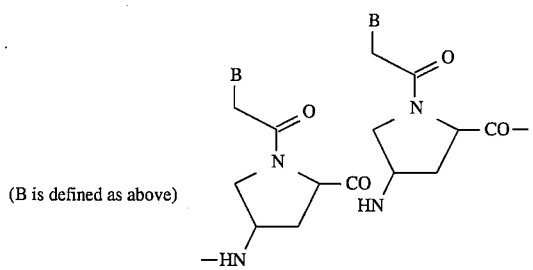

(B is defined as above)

Syntheses of the monomeric building blocks

Monomers for peptide-nucleic acids having a glycylglycine backbone

The synthesis of monomers for glycylglycine compounds is explained using the thymine building block as an example:

N-(Benzyl)ethanolamine 1 is alkylated with tert-butyl bromoacetate 2 in the presence of an auxiliary base to form 3. The hydroxyl group is converted into a leaving group (e.g. to form 4) and substituted by a heterocyclic nucleobase (e.g. to form 5).

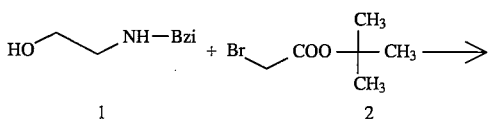

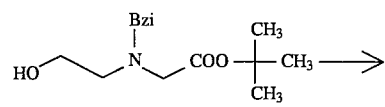

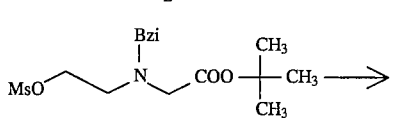

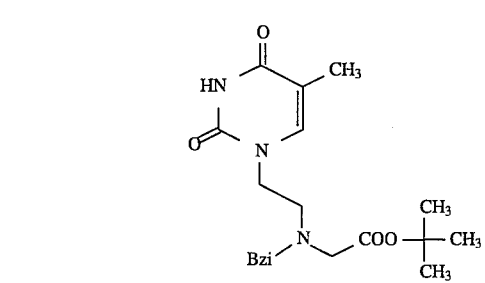

The N-benzyl group is removed hydrogenolytically and the resulting amine, e.g. 6, is subsequently reacted with N-Fmoc-glycine in the presence of a condensing agent, such as N,N'-dicyclohexylcarbodiimide. The resulting dipeptide ester 7 is cleaved with trifluoroacetic acid. The product 8 is suitable for use in peptide solid-phase synthesis under "Fmoc conditions".

The derivatives of other nucleobases can be synthesized in an analogous manner.

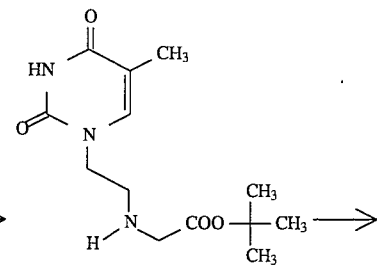

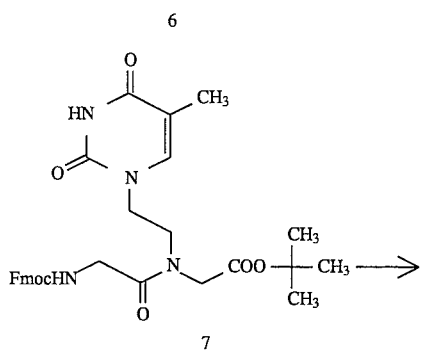

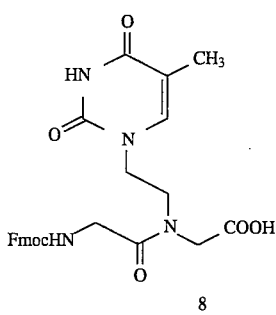

Monomers for peptide-nucleic acids having a 4-aminoproline backbone

The synthesis of monomers for this type of structure may be explained using the thymine derivative of the L-cis series as an example:

trans-N-(Benzyloxycarbonyl)-4-hydroxy-L-proline 9 is converted into the methyl ester 10 using methyl iodide and caesium carbonate. The 4-hydroxyl group in 10 is transformed into a leaving group, e.g. a methyl sulphonate. This results in the formation of 11, for example. Substitution with sodium azide or lithium azide leads, with inversion at C-4, to the cis-4-azido derivative 12. Reduction of the azide function to the amino group in the presence of the N-benzyloxycarbonyl protective group is achieved, for example, using hydrogen sulphide in pyridine/water. Subsequent introduction of a tert-butoxycarbonyl protective group yields the derivative 13, which can be selectively unblocked.

The α-N-benzyloxycarbonyl protective group of the compound 13 can be removed hydrogenolytically. This results in the formation of 14, which is suitable for linking to nucleobases. Thus, for example, reaction of 14 with 1-carboxymethylthymine 15 in the presence of condensing agents, such as, for example, N,N'-dicyclohexylcarbodiimide, affords the thymine compound 16. Basic hydrolysis of the methyl ester leads to the peptide-nucleic acid 17, which is suitable for use in peptide solid-phase synthesis.

If a double inversion is carried out on 10, derivatives of L-trans-4-aminoproline are obtained by an analogous route.

Compounds of the D series can be obtained by starting from D-hydroxyproline.

The derivatives of other nucleobases can be prepared by analogous routes.

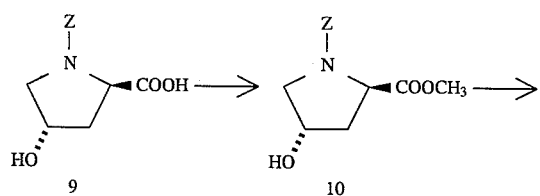
9 → 10

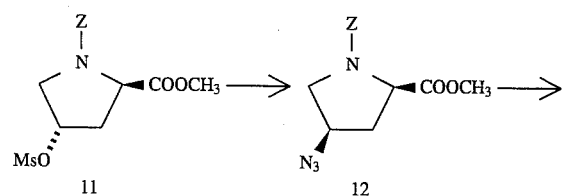
11 → 12

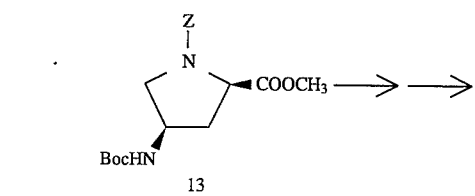
13

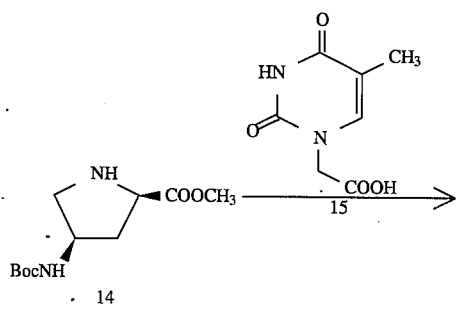
14

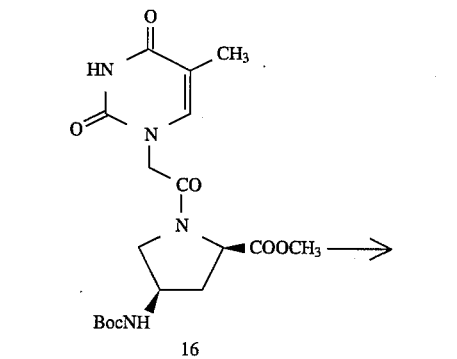
16

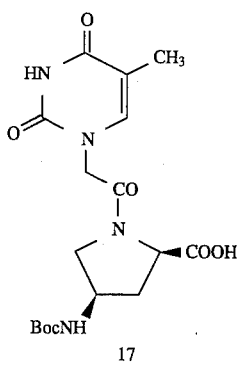
17

Oligomerization

The linking of the building blocks to form oligomers is effected by solid-phase synthesis, preferably on an Applied Biosystems 431-A peptide synthesizer. PAM, MBHA or HMP resins from Applied Biosystems were employed as polymeric supports. The building blocks are linked either by the Fmoc or Boc processes in analogy with conventional peptide synthesis. The building blocks are activated in n-methyl-2-pyrrolidone by reacting with hydroxybenzotriazole/dicyclohexylcarbodiimide or pentafluorophenol/dicyclohexylcarbodiimide. The sequences are subsequently cleaved off by being treated with HF or trifluoromethanesulphonic acids (Boc method, PAM or MBHA resin), or by trifluoroacetic acid (Fmoc method, HMP resin). The reaction products are isolated by preparative HPLC on RP 8 using an ascending gradient of trifluoroacetic acid in acetonitrile/water. The glycylglycine building blocks listed below were preferably employed for the oligomerization:

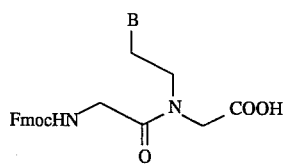 B = 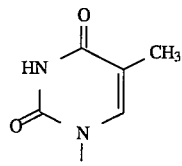 II FmocT

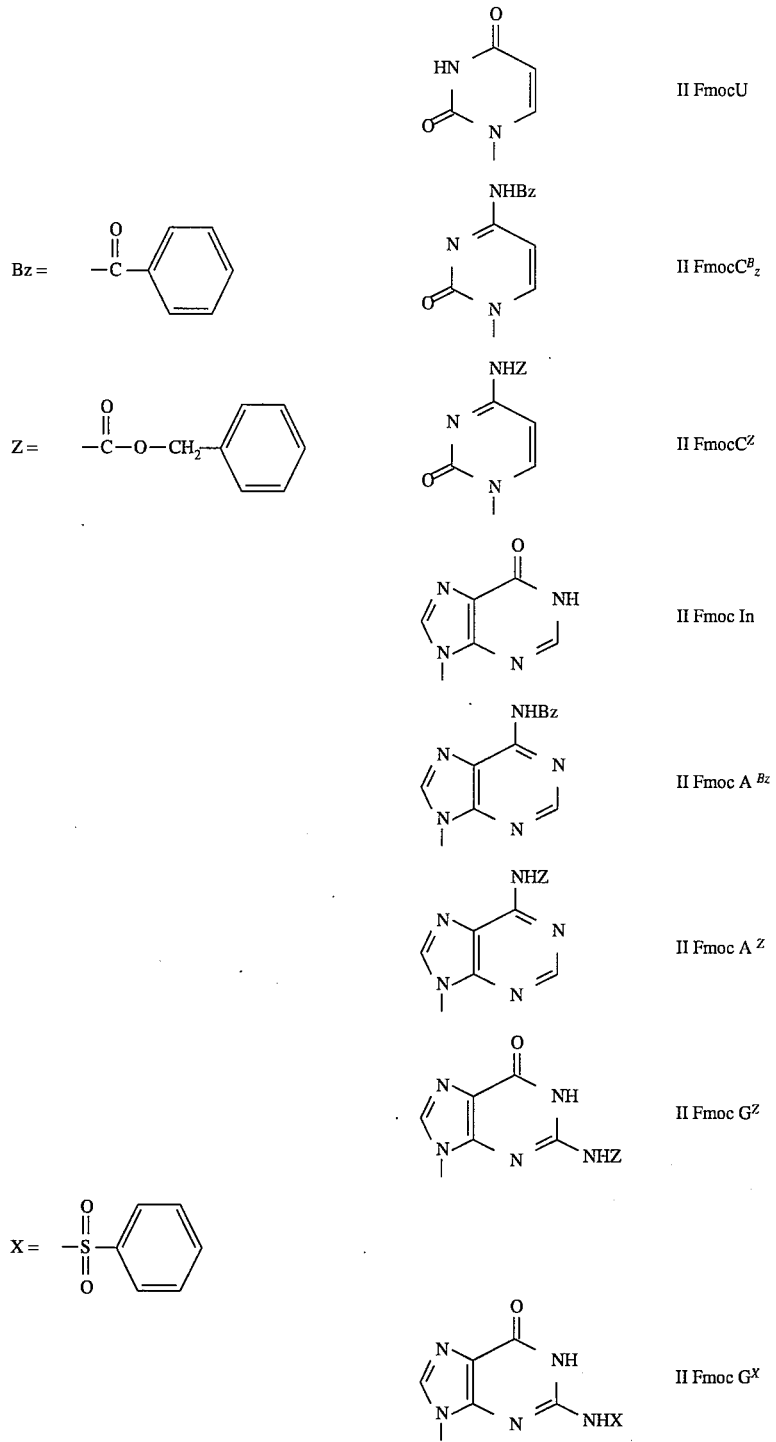
This gives rise to the following glycylglycine synthesis equivalents:
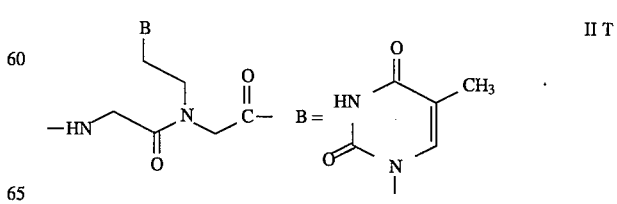

-continued
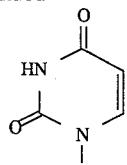 II U
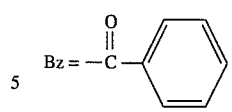 Bz = 
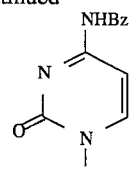 III Boc C$^{Bz}$
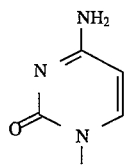 II C
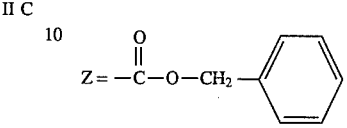 Z = 
III Boc C$^Z$
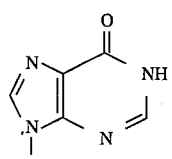 II In
 III Boc In
II A
III Boc A$^{Bz}$
II G$^Z$
 III Boc A$^Z$
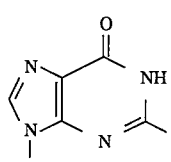
 III Boc G$^Z$
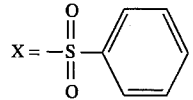 X = 
 III Boc G$^X$
The 4-aminoproline building blocks listed below were preferably employed for the oligomerization:
 III Boc T
X = 
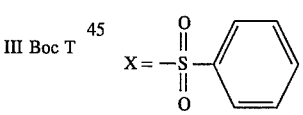
This gives rise to the following 4-aminoproline synthesis equivalents:
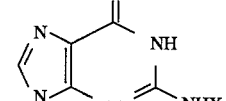 III Boc U
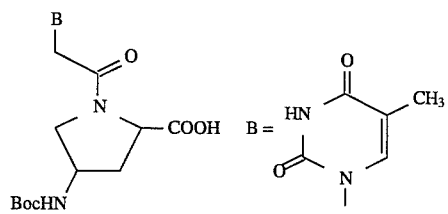
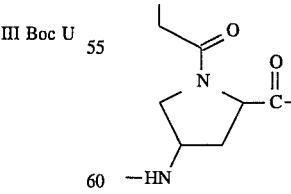 III T
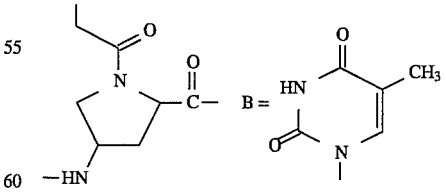

-continued

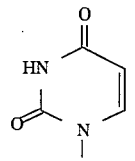
III U

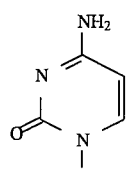
III C

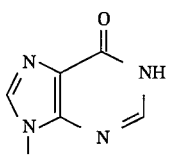
III In

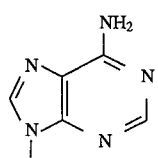
III A

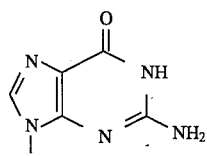
III G

Stability of nucleic acid-binding polymers towards proteases and nucleases

In addition to their chain length, their sequence and their cell permeability, their resistance to proteases and nucleases is of importance for the biological effect of nucleic acid-binding oligomers.

The synthesized oligomers of the aminoproline type were therefore compared with natural oligonucleotide diesters with regard to their stability towards proteases and nucleases.

For this purpose, the nucleic acid-binding oligomers were treated with non-specific and specific proteases, such as, for example, pronase E, proteinase K, trypsin, endoprotease Lys.C, V8 protease, protease IX and protease XXI, nucleases, such as, for example, S1 nuclease and Ba131 nuclease, phosphodiesterase, and cell extracts and organ extracts and blood serum and blood extracts which contain various nucleases and proteases. The oligomers were examined for degradation by polyacrylamide gel electrophoresis and UV shadowing on TLC plates containing UV indicator and by silver-staining the polyacrylamide gels.

Natural oligonucleotide diesters only have a low degree of stability towards nucleases. They are completely degraded within the space of from 30 minutes to 1 hour.

By contrast, nucleic acid-binding oligomers of the amino proline type are completely resistant towards nucleases and proteases and are therefore particularly well suited for use as antisense inhibitors.

Investigations of the binding of the oligomers to nucleic acids

Binding to DNA single strands as determined by gel-shift analyses The nucleic acid-binding oligomers described here were investigated in gel-shift analyses. In these band-shift experiments, the altered migratory behaviour of radioactively labelled DNA diester oligonucleotides was measured by polyacrylamide gel electrophoresis following hybridization to the oligomers described here. Owing to the formation of the hybrid, the hybridized DNA diester oligonucleotides migrate more slowly in the electrophoresis, firstly because the molecular weight is increased and secondly because the relative charge per unit of mass is diminished. As compared to a non-hybridized DNA oligonucleotide, their migration in the gel is retarded.

Strand displacement in double-stranded plasmid DNA

Nucleic acid-binding oligomers, such as, for example, those possessing a 4-aminoproline or glycylglycine backbone, are biologically active in that they exhibit binding, in a sequence-selected manner, to double-stranded DNA (ds DNA) by strand displacement. This effect of nucleic acid-binding oligomers can be demonstrated, in a sequence-dependent and concentration-dependent manner, in in-vitro tests.

Inhibition of gene expression (in-vitro translation test)

Nucleic acid-binding oligomers which proved to be of interest in gel-shift and strand-displacement experiments were tested for their ability to inhibit the protein synthesis determined by specific genes. A prerequisite for this is that the corresponding sequence of the nucleic acid-binding oligomer is contained in the relevant gene in parallel or antiparallel base sequence and that a suitable target sequence in the gene to be inhibited is selected by preliminary experiments, for example using diester oligonucleotides. It emerged in the in-vitro translations that the nucleic acid-binding oligomers described here are very potent, sequence-specific inhibitors of gene expression. Shorter sequences and lower concentrations than those of the diester oligonucleotides were adequate.

Therapeutically active nucleic acid-binding oligomers, as described here, are not only able to inhibit gene expression, as mentioned above, by binding to RNA in a sequence-selective manner, but, naturally, can also inactivate, in a sequence-selective manner, the promotor and enhancer sequences of genes to be inhibited as a result of their property of displacing double-stranded DNA.

For this application in relation to gene inactivation, nucleic acid-binding oligomers contain not only nucleobase sequences of (−)-strand DNA but, under all circumstances, also the (+)-strand DNA sequence of the target DNA to be inhibited.

The target sequence can be derived from the promotor of a disease-producing gene. Target sequences which bind enhancer or transcription factors and DNA polymerase or RNA polymerase and are present in the genes of viruses, bacteria, fungi or endoparasites, or are present in oncogenes or in genes which are involved in the expression of inflammatory disorders, autoimmune disorders, or disorders of the coronary circulation, such as high blood pressure, or arteriosclerosis, may, in particular, be mentioned here as potential target sequences for the therapeutic application of nucleic acid-binding oligomers.

In addition to the nucleic acid-binding oligomers, the corresponding pharmaceutical preparations contain the auxiliary substances, such as, for example, buffers and/or stabilizers or liposome formulations, which are customary for parenteral preparations. Topical application is also conceivable. The preparations which can be employed for this purpose are, for example, ointments, creams, solutions or plasters which, in addition to the active compound, contain the pharmaceutical auxiliary substances which are suitable for this application.

EXAMPLES

Example 1

N-Benzyl-N-(2-hydroxyethyl)-glycine tert-butyl ester (3)

tert-Butyl bromoacetate (32.3 ml; 0.2 mol) is slowly added dropwise, while cooling in ice, to a solution of N-benzylethanolamine (30.2 g; 0.2 mol) and triethylamine (27.9 ml; 0.2 mol) in anhydrous N,N-dimethylformamide (200 ml). The mixture is stirred at room temperature for 22 h and is then concentrated in vacuo. The residue is subsequently distilled repeatedly with toluene. The resulting oil is taken up in dichloromethane (400 ml) and extracted twice by shaking with water (160 ml on each occasion). The organic phase is dried (magnesium sulphate) and concentrated. Yield: 47.8 g (90%), colourless oil.

Example 2

N-Benzyl-N-[2-(methanesulphonyloxy)ethyl]-glycine tert-butyl ester (4)

The product from Example 1 (10.0 g; 38 mmol) is dissolved in anhydrous pyridine (185 ml), and methanesulphonyl chloride (3.7 ml; 46 mmol) is slowly added dropwise at 0° C. The solution is stirred at room temperature for 6.5 h. Subsequently, the solution is diluted with dichloromethane (740 ml) and extracted twice with a 10% solution of sodium hydrogen carbonate (250 ml on each occasion). The organic phase is dried (magnesium sulphate) and concentrated, and the residue is subsequently distilled repeatedly with toluene. Yield: 10.79 g (85%), brown oil.

Example 3

N-Benzyl-N-[2-(thymin-1-yl) ethyl]-glycine tert-butyl ester (5)

The product from Example 2 (10.73 g; 31 mmol), thymine (7.88 g; 62 mmol) and potassium carbonate (8.64 g; 62 mmol) are suspended in anhydrous N,N-dimethylformamide (325 ml). The suspension is stirred at room temperature for 1 h and then at 80° C. for 6 h. The cooled mixture is codistilled repeatedly with toluene, and the residue is taken up in chloroform (500 ml) and extracted twice with water (150 ml on each occasion). The crude product is purified by chromatography on silica gel (eluent: toluene/ethanol, 27:1). Yield: 5.58 g (48%).

Example 4

N-(2-Hydroxyethyl)-glycine tert-butyl ester

The compound is prepared, in analogy with Example 1, from ethanolamine (18.33 g; 0.3 mol) and tert-butyl bromoacetate 58.6 g; 0.3 mol) in the presence of triethylamine (30.7 g; 0.3 mol) in anhydrous N,N-dimethylformamide (300 ml). The crude product is purified by chromatography on silica gel (eluent: chloroform/methanol, 16:1). Yield: 33.65 g (64%).

Example 5

N-Benzyloxycarbonyl-N-(2-hydroxyethyl)-glycine tert-butyl ester

Potassium carbonate (33.0 g; 0.19 mol) is added to a solution of the product from Example 4 (32.15 g; 0.18 mol) in dioxane (1.0 l) and water (0.5 l). A solution of benzyl chloroformate (27.3 ml; 0.19 mol) in dioxane (0.2 l) is slowly added dropwise at room temperature. The solution is stirred at room temperature for 3.5 h and subsequently concentrated. The residue is taken up in dichloromethane (3.0 l) and extracted by shaking with water (1.0 l). The aqueous phase is re-extracted five times with dichloromethane. The organic phases are combined, dried (magnesium sulphate) and concentrated. Yield: 24.47 g (43%), pale yellow oil.

Example 6

N-Benzyloxycarbonyl-N-[2-(methanesulphonyloxy)ethyl]-glycine tert-butyl ester

The product from Example 5 (14.4 g; 47 mmol) is reacted in anhydrous pyridine (270 ml) with methanesulphonyl chloride (4.47 ml; 58 mmol) and then worked up as described in Example 2. Yield: 14.7 g (82%), brown oil.

Example 7

N-Benzyloxycarbonyl-N-(2-thymin-1-yl)-glycine tert-butyl ester

The product from Example 6 (8.47 g; 22 mmol) is reacted, in accordance with the process specified in Example 3, with thymine (5.51 g; 44 mmol) in the presence of potassium carbonate (6.06 g; 44 mmol) in N,N-dimethylformamide (220 ml) as the solvent. Chromatographic purification is carried out using toluene/ethanol (15:1) as the eluent. Yield: 3.19 g (35%).

Example 8

N-[2-(Thymin-1-yl)ethyl]-glycine tert-butyl ester (6)

a) The product from Example 3 (5.56 g; 15 mmol) is hydrogenated for 5 h, at room temperature and under atmospheric pressure, in anhydrous methanol (75 mol) over palladium/active charcoal (10%; 2.76 g). The catalyst is filtered off from the solution with suction, and the solution is then concentrated in vacuo. Yield: 3.82 g (91%).

b) The product from Example 6 (2.76 g; 7 mmol) is hydrogenated for 21 h, at room temperature and under atmospheric pressure, in methanol (108 ml)/dioxane (7 ml) over palladium on barium sulphate (5%; 1.38 g). At the end of this time, the same quantity of catalyst is added once again and hydrogenation is continued for a further 7.5 h. Subsequent working up is carried out as described under a). Yield: 1.9 g (quantitative).

Example 9

N-[N'-(Fluorenylmethyloxycarbonyl)glycyl]-N-[2-(thymin-1-yl)ethyl]-glycine tert-butyl ester (7)

The product from Example 8 (3.78 g; 13 mmol) and N-(fluorenylmethyloxycarbonyl)glycine (5.9 g; 20 mmol) are dissolved in anhydrous N,N-dimethylformamide (160 ml) under a protective atmosphere of argon gas. N,N'-Dicyclohexylcarbodiimide (4.11 g; 20 mmol) is added in portions at 0° C. The mixture is stirred at room temperature for 21 h and the solid which has precipitated is subsequently filtered off with suction. The solution is then concentrated in vacuo, and subsequently distilled repeatedly with toluene, and the crude product is chromatographed on silica gel. (Eluent: toluene/ethanol, 30:1-20:1). Yield: 6.33 g (82%).

Example 10

N-[N'-(Fluorenylmethyloxycarbonyl)glycyl]-N-[2-(thymin-1-yl)ethyl]-glycine (8) The tert-butyl ester from Example 9 (6.31 g; 11 mmol) is left to stand at room temperature for 7 h in 100% formic acid (105 ml). The solution is subsequently codistilled with toluene and twice with methanol (200 ml on each occasion). The product crystallizes from methanol. Yield: 5.43 g (96%).

Example 11

N-Benzyloxycarbonyl-4-hydroxy-L-trans-proline methyl ester (10)

A solution of N-benzyloxycarbonyl-4-hydroxy-L-trans-proline 9 (47.5 g; 179 mmol) in anhydrous methanol (900 ml) is adjusted to pH=9.0-9.5 using caesium carbonate. The mixture is subsequently stirred at room temperature for 30 min., and then concentrated. After having been dried for 30 minutes under high vacuum, the residue is taken up in anhydrous N,N-dimethylformamide (900 ml). Iodomethane (28.0 g; 197 mmol) is added, and the mixture is stirred at room temperature for 21 h. The solution is concentrated, and the residue is subsequently distilled repeatedly with toluene, taken up in chloroform (1.8 l), and then extracted by shaking once with each of water and a 10% solution of sodium hydrogen carbonate, and once again with water (600 ml on each occasion). The organic phase is dried (magnesium sulphate) and concentrated. Yield: 50.0 g (quantitative).

Example 12

N-Benzyloxycarbonyl-4-methanesulphonyloxy-L-trans-proline methyl ester (11)

The product from Example 11 (50.0 g; 178 mmol) is dissolved in anhydrous pyridine (910 ml). Methanesulphonyl chloride (18.6 ml; 241 mmol) is added dropwise while cooling in ice. Subsequently, the solution is stirred for 2.5 h during which it is allowed to warm to room temperature. The solution is then diluted with dichloromethane (3.6 l) and extracted twice by shaking with a 10% solution of sodium hydrogen carbonate (1.1 l on each occasion). The organic phase is dried (magnesium sulphate), concentrated and the residue subsequently distilled repeatedly with toluene. Yield: 64.0 g (quantitative).

Example 13

4-Azido-N-benzyloxycarbonyl-L-cis-proline methyl ester (12)

The methanesulphonate (64.0 g; 178 mmol) obtained in Example 12 is dissolved in anhydrous N,N-dimethylformamide (1.8 l), and lithium azide (43.8 g; 895 mmol) is added and the mixture is then stirred at 50° C. for 24 h. The reaction solution is concentrated in vacuo, and the residue is subsequently distilled repeatedly with toluene, taken up in ethyl acetate (1.8 l) and extracted twice with water (600 ml on each occasion). The organic phase is dried (magnesium sulphate) and concentrated. Yield: 50.5 g (93 %)

Example 14

N-Benzyloxycarbonyl-4-tert -butyloxycarbonylamino-L-cis-proline methyl ester (13)

A solution of the azido compound from Example 13 (52.0 g; 0.17 mol) in pyridine/water (5:1; 1.02 l) is saturated with hydrogen sulphide at 0° C. The solution is left at room temperature for 16 h and subsequently concentrated in vacuo. The residue is taken up in as little ethanol as possible, and precipitating impurities are repeatedly filtered off. The ethanol solution is concentrated and dried under high vacuum for 16 h. The resulting crude product is dissolved in dioxane (850 ml) and ethyl diisopropylamine (42.6 ml; 0.24 mol) and di-tert-butyl dicarbonate (56.2 g; 0.26 mol) are then added, and the mixture is stirred at room temperature for 3 h. The resulting mixture is concentrated in vacuo. The residue is taken up in dichloromethane (1.7 l) and extracted once by shaking with a 0.5 N solution of citric acid (600 ml). The aqueous phase is re-extracted three times with dichloromethane. The combined organic phases are dried (magnesium sulphate) and concentrated. The crude product is purified by chromatography on silica gel (eluent: toluene/ethanol, 22:1). Yield: 34.9 g (54%).

Example 15

4-tert-Butyloxycarbonylamino-L-cis-proline methyl ester (14)

The product from Example 14 (12.3 g; 32 mmol) is hydrogenated for 2.5 h, at room temperature and under atmospheric pressure, in methanol (320 ml) over palladium/active charcoal (10%; 6.2 g). Once reaction is complete, the catalyst is filtered off with suction and the solution is concentrated. Yield: 7.2 g (91%).

Example 16

4-tert-Butyloxycarbonylamino-N-[(thymin-1-yl)-acetyl]-L-cis-proline methyl ester (15)

1-Carboxymethyl-thymine (7.82 g; 43 mmol) is added to a solution of the product from Example 15 (6.97 g; 29 mmol) in anhydrous N,N-dimethylformamide (340 ml). N,N'-Dicyclohexylcarbodiimide (8.82 g; 43 mmol) is then added, while cooling in ice, and the solution is subsequently stirred for 2.5 h during which it warms to room temperature. The precipitated solid is filtered off with suction, and the solution is concentrated in vacuo and the residue subsequently distilled repeatedly with toluene. The crude product is purified by chromatography (eluent: toluene/ethanol, 7:1). Yield: 10.44 g (89%).

Example 17

4-tert-Butyloxycarbonylamino-N-[(thymin-1-yl) acetyl]-L-cis-proline (16)

Lithium hydroxide hydrate (50 mg; 1.2 mmol) is added to a solution of the product from Example 16 (410 mg; 1.0 mmol) in dioxane/water (5:1; 7 ml), and the mixture is stirred at room temperature for 5 h. The same quantity of lithium hydroxide hydrate is then added once again and the mixture is left at room temperature for a further 2 h. The solution is neutralized with 0.5 N hydrochloric acid and concentrated. The product crystallizes from methanol. Yield: 195 mg (49%).

Example 18

$N^4$-Benzoyl-1-tert-butyloxycarbonylmethylcytosine tert-Butyl bromoacetate (24 ml; 0.15 mol) is slowly added dropwise, at room temperature, to a suspension of $N^4$-benzoylcytosine (21.5 g; 0.1 mol) and potassium carbonate 13.8 g; 0.1 mol) in anhydrous N,N-dimethylformamide (2.15 l). The heterogeneous mixture is stirred vigorously at room temperature for 20 h and insoluble starting material is subsequently filtered off with suction; the filtrate is concentrated in vacuo and the residue is subsequently distilled repeatedly with toluene and then taken up in chloroform (1.0 l); it is then extracted once by shaking with water (0.3 l), and the phases are swiftly separated. The organic phase is filtered once more and concentrated. Yield: 15.23.g (46%).

Example 19

$N^4$-Benzoyl-1-carboxymethylcytosine

The product from Example 18 is dissolved in trifluoroacetic acid (170 ml) and left at room temperature for 1 h 45 min. Subsequently, the mixture is codistilled five times with toluene and the product is dried in a desiccator over phosphorus pentoxide/potassium hydroxide for 24 h. Yield: 11.8 g (93%).

Example 20

N-[($N^4$-Benzoylcytosin-1-yl)acetyl]-4-tert-butyloxycarbonylamino-L-cis-proline methyl ester N,N'-Dicyclohexylcarbodiimide (8.67 g; 42 mmol) is added, while cooling in ice, to a solution of $N^4$-benzoyl-1-carboxymethylcytosine (11.46 g; 42 mmol) and 4-tert-butyloxycarbonylamino-L-cis-proline methyl ester (6.85 g; 28 mmol) in anhydrous N,N-dimethylformamide (340 ml), and the solution is stirred for 2 h during which it warms to room temperature. The precipitated solid is then filtered off with suction, and the filtrate is concentrated and the residue subsequently distilled repeatedly with toluene. The crude product is purified by chromatography (eluent: toluene/ethanol, 8:1). Yield: 3.80 g (27%).

Example 21

N-[($N^4$-Benzoylcytosin-1-yl) acetyl]-4- tert-butyloxycarbonylamino-L-cis-proline The product from Example 20 (2.68 g; 5.4 mmol) is dissolved in methanol (54 ml), and 1 N sodium hydroxide solution (6.3 ml) is added, and the mixture is stirred at room temperature for 18 h. Subsequently, the mixture is neutralized with 0.5 N hydrochloric acid and concentrated. The product crystallizes from methanol. Yield: 2.44 g (94%).

Example 22

N-Benzyloxycarbonyl-4-nitrobenzoyloxy-L-cis-proline methyl ester

3.29 g (11.8 mmol) of Z-L-trans-hydroxyproline methyl ester are dissolved in 50 ml of abs. THF. 3.76 g (14.3 mmol) of triphenylphosphine and 2.19 g (13.1 mmol) of p-nitrobenzoic acid are then added in succession at room temperature. The mixture is cooled down to 0° C. and 2.5 g (14.3 mmol) of DEAD in abs. THF are added dropwise at this temperature. The mixture is subsequently stirred at room temperature overnight. It is then concentrated under high vacuum and the residue is chromatographed on silica gel (eluent, ethyl acetate/hexane, 2:1). Yield: 3.34 g (66.2% of theory) $R_f$: 0.68, eluent, ethyl acetate/hexane (2:1)

Example 23

N-Benzyloxycarbonyl-4-hydroxy-L-cis-proline methyl ester

2.71 g (6.2 mmol) of N-benzyloxycarbonyl-4-nitrobenzoyl-oxy-L-cis-proline methyl ester are dissolved in 600 ml of abs. methanol. Subsequently, a solution of 0.34 g (6.3 mmol) of sodium methoxide in $CH_3OH$ is added dropwise within the space of 5 min. The mixture is subsequently stirred at room temperature for 30 min. and after that dilute hydrochloric acid is added until the pH is 5–6. The mixture is concentrated and a saturated solution of sodium chloride is added to the residue and this mixture is extracted 2 x by shaking with ethyl acetate. The organic phase is dried over $Na_2SO_4$, filtered, concentrated and chromatographed on silica gel (eluent, ethyl acetate/hexane, 2:1). Yield: 1.52 g (86.0 % of theory) $R_f$: 0.28, eluent, ethyl acetate/hexane (2:1)

Example 24

N-Benzyloxycarbonyl-4-methanesulphonyloxy-L-cis-proline methyl ester

1.59 g (5.7 mmol) of N-benzyloxycarbonyl-4-hydroxy-L-cis-proline methyl ester are dissolved in 50 ml of abs. pyridine and cooled to 0° C. 0.6 ml (7.7 mmol) of methanesulphonyl chloride is added dropwise at 0° C., and the mixture is subsequently stirred at room temperature for 3 hours. The mixture is then concentrated and 100 ml of methylene chloride are added to the residue, and this latter mixture is then extracted 2 x by shaking with a 10% solution of $NaHCO_3$, dried over sodium sulphate and concentrated once again, with the residue being subsequently distilled repeatedly with toluene. Yield: quantitative $R_f$: 0.33, eluent, toluene/EtOH (10:1)

Example 25

4-Azido-N-benzyloxycarbonyl-L-trans-proline methyl ester

2.01 g (5.6 mmol) of N-benzyloxycarbonyl-4-methanesulphonyloxy-L-cis-proline methyl ester are dissolved in 50 ml of abs. DMF, and 1.37 g (28 mmol) of lithium azide are added at room temperature. After that, the mixture is stirred at 50° C. for 24 h. The mixture is then concentrated in vacuo and the residue is subsequently distilled repeatedly with toluene. The residue is taken up in ethyl acetate and extracted 2 x with water, and the organic phase is then dried over $Na_2SO_4$ and concentrated once again. Yield: 1.66 g (97% of theory) $R_f$: 0,58, eluent, toluene/EtOH (10:1)

Example 26

N-Benzyloxycarbonyl-4-tert-butoxycarbonylamino-L-trans-proline methyl ester

A solution of 1.59 g (5.2 mmol) of 4-azido-N-benzyloxycarbonyl-L-trans-proline methyl ester in 27 ml of pyridine and 5.3 ml of water is saturated with hydrogen sulphide at 0° C. The mixture is left stirring at room temperature for 45 min., and excess $H_2S$ is then driven off with nitrogen and the mixture is concentrated in vacuo with the residue subsequently being distilled repeatedly with toluene. The residue is taken up in 30 ml of ethanol and precipitating impurities are filtered off. The mother liquor is concentrated once again and is dried overnight under high vacuum. The resulting crude product is dissolved in 30 ml of dioxane (abs.) and 1.32 ml of ethyldiisopropylamine and 1.73 g of $BOC_2O$ are added. This mixture is then stirred at room temperature for 3 h and then concentrated in vacuo. The residue is taken up in 50 ml of $CH_2Cl_2$, and extracted once by shaking with 0.5 N citric acid, and the aqueous phase is subsequently extracted a further 3 x with $CH_2Cl_2$. The combined organic phases are dried over $Na_2SO_4$, filtered and concentrated, and the remaining oil is chromatographed on silica gel (eluent, toluene/EtOH, 25:1). Yield: 1.65 g (83.7% of theory) $R_f$: 0,44, eluent, toluene/EtOH (10:1)

Example 27

4-tert-Butyloxycarbonylamino-L-trans-proline methyl ester

2.95 g (7.7 mmol) of N-benzyloxycarbonyl-4-tert-butyloxycarbonylamino-L-trans-proline methyl ester are dissolved in 80 ml of abs. methanol and hydrogenated for 2.5 h, at room temperature and under atmospheric pressure, over palladium/active charcoal (10%, 1.45 g). Once reaction is complete (monitoring with TLC, toluene/EtOH, 8:1), the catalyst is filtered off with suction and the filtrate is concentrated. Yield: 1.75 g (92.1% of theory) $R_f$: 0,23, eluent, toluene/EtOH (8:1)

Example 28

4-tert-Butyloxycarbonylamino-N-[(thymin-1-yl)-acetyl]-L-trans-proline methyl ester

275 mg (1.5 mmol) of 1-carboxy-methylthymine are dissolved in 10 ml of abs. DMF, cooled to −30° C., and 230 mg (1.7 mmol) of HOBT×$H_2O$ and 330 mg (1.7 mmol) of EDCL×HCl are added at this temperature. The mixture is then subsequently stirred at −30° C. for 15 min, and a suspension of 245 mg (1 mmol) of 4-tertbutyloxycarbonylamino-L-trans-proline methyl ester in 10 ml of DMF and 0.41 ml (3 mmol) of triethylamine is added at −30° C. The mixture is stirred at −30° C. for one hour and subsequently placed at room temperature for 24 h. It is then concentrated and the residue taken up in ethyl acetate and extracted in turn with 1 N HCl, a saturated solution of $NaHCO_3$ and a saturated solution of NaCl. The organic phase is dried over $Na_2SO_4$, filtered and concentrated. Yield: 300 mg (73.1% of theory) $R_f$: 0,16, eluent, toluene/EtOH (8:1)

Example 29

4-tert-Butyloxycarbonylamino-N-[(thymin-1-yl)-acetyl]-L-trans-proline 50 mg (1.2 mmol) of LiOH×$H_2O$ are added to a solution of 410 mg (1 mmol) of 4-tert-butyloxycarbonylamino-N-[(thymin-1-yl)-acetyl]-L-trans-proline methyl ester in 6 ml of dioxane and 1.2 ml of $H_2O$, and the mixture is stirred at room temperature for 5 hours. After that, a further 50 mg of LiOH×$H_2O$ are added and the mixture is stirred for a further 2 hours. The solution is neutralized with 0.5 N HCl and concentrated, with the residue subsequently being distilled repeatedly with toluene and then boiled up with isopropanol, filtered off with suction from the hot mixture, and washed with ether. Yield: 375 mg (91.4% of theory) $R_f$: 0,24, eluent, $CH_2Cl_2/CH_3OH$ (2:1)

Example 30

4-tert-Butyloxycarbonylamino-N-[($N^4$-benzyloxycarbonylcytosin-1-yl)-acetyl]-L-cis-proline methyl ester

454 mg (1.5 mmol) of 4-tert-butyloxycarbonylamino-L-cis-proline methyl ester are dissolved in 10 ml of abs. DMF and cooled to −30° C. 230 mg (1.7 mmol) of HOBT and 330 mg (1.7 mmol) of EDC are added at this temperature, and the mixture is subsequently stirred at −30° C. for 15 min. A solution of 245 g of $N^4$-benzyloxycarbonyl-1-carboxymethylcytosine in 10 ml of abs. DMF and 0.41 ml (3 mmol) of triethylamine is then added dropwise (at −30° C.) and the suspension is subsequently stirred at this temperature for 1 hour. It is then allowed to warm to room temperature and is stirred overnight. The solution is then concentrated under high vacuum, and ethyl acetate is added. After that, the mixture is extracted 1 x with 1 N HCl, 1 x with a solution of Na bicarbonate, and 1 x with a solution of NaCl. The organic portion is dried over $Na_2SO_4$, filtered and concentrated. Yield: 460 mg (86.9% of theory) $R_f$: 0,57, eluent, $CH_2Cl_2/CH_3OH$ (10:1)

Example 31

4-tert-Butyloxycarbonylamino-N-[($N^6$-benzyloxycarbonylcytosin-1-yl)-acetyl]-L-cis-proline 440 mg (0.83 mmol) of 4-tert-butyloxycarbonylamino-N-[($N^4$-benzyloxycarbonylcytosin-1-yl)-acetyl]-L-cis-proline methyl ester are dissolved in 6 ml of abs. dioxane and 1.2 ml of $H_2O$. 42 mg (1 mmol) of $LiOH\times H_2O$ are added to this solution, and the mixture is stirred at room temperature for 5 hours. After that, a further 42 mg of $LiOH\times H_2O$ are added, and stirring is continued for a further 2 hours. The solution is then neutralized with 0.5 N HCl and subsequently concentrated, with the residue being redistilled repeatedly with toluene. The crystalline residue is boiled for about 10 min. with isopropanol and then filtered off with suction from the hot mixture and washed with ether. Yield: 250 mg (58.4% of theory) $R_f$: 0,57, eluent, $CH_2Cl_2/CH_3OH$ (2:1)

Example 32

4-tert-Butyloxycarbonylamino-N-[($N^6$-benzyloxycarbonyladenin-9-yl)-acetyl]-L-cis-proline methyl ester 327 mg (1.0 mmol) of $N^6$-benzyloxycarbonyl-9-carboxymethyladenine are dissolved in 610 ml of abs. DMF and cooled to −30° C. 175 mg (1.3 mmol) of HOBT and 248 mg (1.3 mmol) of EDCI are added at this temperature and the mixture is left stirring at −30° C. for a further 15 min. A solution of 732 mg (3 mmol) of 4-tert-butyloxycarbonylamino-L-cis-proline methyl ester in 10 ml of abs. DMF and 0.41 ml (3 mmol) of triethylamine is then added dropwise at −30° C. The mixture is subsequently stirred at −30° C. for a further 1 hour and after that is stirred at room temperature overnight. Once concentration under high vacuum has taken place, ethyl acetate is added to the residue and this mixture is extracted 1 x with 1 N HCl, 1 x with a solution of Na bicarbonate and 1 x with a solution of NaCl. The organic phase is dried over $Na_2SO_4$, filtered and concentrated. Yield: 360 mg (65% of theory) $R_f$: 0,86, eluent, $CH_2Cl_2/CH_3OH$ (4:1)

Example 33

4-tert-Butyloxycarbonylamino-N-[($N^6$-benzyloxycarbonyladenin-9-yl)-acetyl]-L-cis-proline 1.43 g (2.58 mmol) of 4-tert-butyloxycarbonylamino-N-[($N^6$-benzyloxycarbonyladenin-9-yl)-acetyl]-L-cis-proline methyl ester are dissolved in 24 ml of dioxane and 4.8 ml of $H_2O$. 126 mg (3.09 mmol) of $LiOH\times H_2O$ are added to this solution, and the mixture is stirred at room temperature for 5 hours. After that, a further 126 mg of $LiOH\times H_2O$ are added and the mixture is stirred for a further 2 hours. The solution is then neutralized with 0.5 N HCl and concentrated, with the residue being redistilled repeatedly with toluene. The crystalline residue is boiled with isopropanol for about 10 min., filtered off with suction from the hot mixture, and washed well with ether and dried. Yield: 100 mg (43.1% of theory) $R_f$: 0,81, eluent, $CH_2Cl_2/CH_3OH$ (8:1)

Example 34

4- tert-Butyloxycarbonylamino-N-[($N^6$-benzyloxycarbonyladenin-9-yl)-acetyl]-L-trans-proline methyl ester 327 mg (1.0 mmol) of $N^6$-benzyloxycarbonyl-9-carboxymethyladenine are dissolved in 10 ml of abs. DMF and cooled to −30° C. 175 mg (1.3 mmol) of HOBT and 248 mg (1.3 mmol) of EDCI are added at this temperature and the mixture is left stirring at −30° C. for a further 15 min. A solution of 732 mg (3 mmol) of 4-tert-butyloxycarbonylamino-L-trans-proline methyl ester in 10 ml of abs. DMF and 0.41 ml (3 mmol) of triethylamine is then added dropwise at −30° C. The mixture is subsequently stirred at −30° C. for a further 1 hour and after that stirred at room temperature overnight. Once concentration has taken place under high vacuum, ethyl acetate is added to the residue and this mixture is extracted 1 x with 1 N HCl, 1 x with a solution of Na bicarbonate and 1 x with a solution of NaCl. The organic phase is dried over $Na_2SO_4$, filtered and concentrated. Yield: 360 mg (65% of theory) $R_f$: 0,88, eluent, $CH_2Cl_2/CH_3OH$ (4:1)

Example 35

4-tert-Butyloxycarbonylamino-N-[($N^6$-benzyloxycarbonyladenin-9-yl)acetyl]-L-trans-proline 1.22 g (2.20 mmol) of 4-tert-butyloxycarbonylamino-N-[($N^6$-benzyloxycarbonyladenin-9-yl)-acetyl]-L-trans-proline methyl ester are dissolved in 20 ml of dioxane and 4 ml of $H_2O$. 107 mg (2.64 mmol) of $LiOH\times H_2O$ are added to this solution and the mixture is stirred at room temperature for 5 hours. After that, a further 107 mg of $LiOH\times H_2O$ are added and the mixture is stirred for a further 2 hours. The solution is then neutralized with 0.5 N HCl and concentrated, with the residue being redistilled repeatedly with toluene. The crystalline residue is boiled in isopropanol, filtered off with suction from the hot mixture, and washed well with ether and dried. Yield: 720 mg (61% of theory) $R_f$: 0.8, eluent, $CH_2Cl_2/CH_3OH$ (4:1)

Example 36

4-tert-Butyloxycarbonylamino-N-[($N^4$-benzyloxycarbonylcytosin-1-yl)-acetyl]-L-trans-proline methyl ester 454 mg (1.5 mmol) of $N^4$-benzyloxycarbonyl-1-carboxymethylcytosine are dissolved in 10 ml of abs. DMF and cooled to −30° C. 230 mg (1.7 mmol) of HOBT and 330 mg (1.7 mmol) of EDCI are added at this temperature and the mixture is subsequently stirred at −30° C. for a further 15 min. A solution of 245 mg (1 mmol) of 4-tert-butyloxycarbonylamino-L-trans-proline methyl ester in 10 ml of abs. DMF and 0.41 ml. (3 mmol) of triethylamine is then added dropwise at −30° C. and the suspension is subsequently stirred at this temperature for 1 hour. The mixture is then allowed to warm to room temperature and is stirred overnight. The solution is then concentrated under high vacuum and ethyl acetate is added. After that, this mixture is extracted 1 x with 1 N HCl, 1 x with a solution of Na bicarbonate and 1 x with a solution of NaCl. The organic portion is dried over $Na_2SO_4$, filtered and concentrated. The residue is purified by chromatography on silica gel. Eluent, $CH_2Cl_2/CH_3OH$, 10:1). Yield: 480 mg (90.7% of theory) $R_f$: 0,59, eluent, $CH_2Cl_2/CH_3OH$ (10:1)

Example 37

4-tert-Butyloxycarbonylamino-N-[($N^4$-benzyloxycarbonylcytosin-1-yl)-acetyl]-L-trans-proline 450 mg (0.85 mmol) of 4-tert-butyloxycarbonylamino-N-[($N^4$-benzyloxycarbonylcytosin-1-yl)-acetyl]-L-trans-proline methyl ester are dissolved in 6 ml of dioxane and 1.2 ml of $H_2O$. 42 mg (1 mmol) of $LiOH\times H_2O$ are added to this solution and the mixture is stirred at room temperature for 5 hours. After that, a further 427 mg of $LiOH\times H_2O$ are added and the mixture is stirred for a further 2 hours. The solution is then neutralized with 0.5 N HCl and concentrated, with the residue being redistilled repeatedly with toluene. The crystalline residue is boiled with isopropanol, filtered off with suction from the hot mixture, and washed with ether. Yield: 340 mg (77.6% of theory) $R_f$: 0,30, eluent, $CH_2Cl_2$/$CH_3OH$ (2:1)

Example 38

Solid-phase synthesis of H—(II T)$_2$—Ala—OH 192 mg (0.1 mmol) of N-fluorenylmethoxycarbonyl-alanine-HMP resin are initially introduced into a reaction vessel. Prior to each coupling step, the N-fluorenylmethoxycarbonyl protective group is cleaved off by treatment with piperidine. In each case, 253 mg (0.5 mmol) of IIFmocT are activated by reaction with 135 mg (1.0 mmol) of hydroxybenzotriazole and 206 mg (1.0 mmol) of dicyclohexylcarbodiimide in N-methyl-2-pyrrolidone. The step-wise coupling to the polymeric support then takes place. After the last coupling, the N-fluorenylmethoxycarbonyl protective group is removed by treating with piperidine. Cleavage from the support is effected by treating for 60 minutes with trifluoroacetic acid. Purification is effected by RP-HPLC on C8 using an ascending gradient of TFA in acetonitrile. Yield: 12 mg (19%).

Example 39

Solid-phase synthesis of H—(II T)$_8$—Ala—OH 192 mg (0.1 mmol) of N-fluorenylmethoxycarbonyl-alanine-HMP resin are initially introduced into a reaction vessel. Prior to each coupling step, the N-fluorenylmethoxycarbonyl protective group is cleaved off by treatment with piperidine. In each case, 253 mg (0.5 mmol) of IIFmocT are activated by reaction with 135 mg (1.0 mmol) of hydroxybenzotriazole and 206 mg (1.0 mmol) of dicyclohexylcarbodiimide in N-methyl-2-pyrrolidone. The step-wise coupling to the polymeric support then takes place. After the last coupling, the N-fluorenylmethoxycarbonyl protective group is removed by treating with piperidine. Cleavage from the support is effected by treating for 60 minutes with trifluoroacetic acid. Purification is effected by RP-HPLC on C8 using an ascending gradient of TFA in acetonitrile. Yield: 133 mg (60%).

Example 40

Solid-phase synthesis of H—(III T)$_2$—Ala—OH 125 mg (0.1 mmol) of tert-butyloxycarbonyl-alanine-PAM resin are initially introduced into a reaction vessel. Prior to each coupling step, the tert-butyloxycarbonyl protective group is cleaved off by treatment with trifluoroacetic acid. In each case, 200 mg (0.5 mmol) of IIIBocT are activated by reaction with 365 mg (2.7 mmol) of hydroxybenzotriazole and 206 mg (1.0 mmol) of dicyclohexylcarbodiimide in N-methyl-2-pyrrolidone. The stepwise coupling to the polymeric support then takes place. After the last coupling, the tert-butyloxycarbonyl protective group is removed by treating with trifluoroacetic acid. Cleavage from the support is effected by a 25-minute treatment with a solution of 200 μl of trifluoromethanesulphonic acid in 2 ml of trifluoroacetic acid. Purification is effected by RP-HPLC on C8 using an ascending gradient of TFA in acetonitrile. Yield: 29 mg (45%).

Example 41

Solid-phase synthesis of H—(III T)$_8$—Ala—OH 125 mg (0.1 mmol) of tert-butyloxycarbonyl-alanine-PAM resin are initially introduced into a reaction vessel. Prior to each coupling step, the tert-butyloxycarbonyl protective group is cleaved off by treatment with trifluoroacetic acid. In each case, 200 mg (0.5 mmol) of IIIBocT are activated by reaction with 365 mg (2.7 mmol) of hydroxybenzotriazole and 206 mg (1.0 mmol) of dicyclohexylcarbodiimide in N-methyl-2-pyrrolidone. The stepwise coupling to the polymeric support then takes place. After the last coupling, the tert-butyloxycarbonyl protective group is removed by treating with trifluoroacetic acid. Cleavage from the support is effected by a 25-minute treatment with a solution of 200 μl of trifluoromethanesulphonic acid in 2 ml of trifluoroacetic acid. Purification is effected by RP-HPLC on C8 using an ascending gradient of TFA in acetonitrile. Yield: 47 mg (20%).

Example 42

Solid-phase synthesis of H—(III T)$_{12}$—Ala—OH 164 mg (0.1 mmol) of tert-butyloxycarbonyl-2-chlorobenzyloxycarbonyl-lysine-PAM resin are initially introduced into a reaction vessel. Prior to each coupling step, the tert-butyloxycarbonyl protective group is cleaved off by treatment with trifluoroacetic acid. In each case, 200 mg (0.5 mmol) of IIIBocT are activated by reaction with 365 mg (2.7 mmol) of hydroxybenzotriazole and 206 mg (1.0 mmol) of dicyclohexylcarbodiimide in N-methyl-2-pyrrolidone. The step-wise coupling to the polymeric support then takes place. After the last coupling, the tert-butyloxycarbonyl protective group is removed by treating with trifluoroacetic acid. Cleavage from the support is effected by a 25-minute treatment with a solution of 200 μl of trifluoromethanesulphonic acid in 2 ml of trifluoroacetic acid. Purification is effected by RP-HPLC on C8 using an ascending gradient of TFA in acetonitrile. Yield: 174 mg (50%).

Example 43

Solid-phase synthesis of H—(III C-III T)—Ala—OH 125 mg (0.1 mmol) of tert-butyloxycarbonyl-alanine-PAM resin are initially introduced into a reaction vessel. Prior to each coupling step, the tert-butyloxycarbonyl protective group is cleaved off by treatment with trifluoroacetic acid. In each case, 243 mg (0.5 mmol) of IIIBocC$^{Bx}$ and 200 mg (0.5 mmol) of IIIBocT are activated by reaction with 365 mg (2.7 mmol) of hydroxybenzotriazole and 206 mg (1.0 mmol) of dicyclohexylcarbodiimide in N-methyl-2-pyrrolidone. The step-wise coupling to the polymeric support then takes place. After the last coupling, the tert-butyloxycarbonyl protective group is removed by treating with trifluoroacetic acid. Cleavage from the support is effected by a 25-minute treatment with a solution of 200 μl of trifluoromethanesulphonic acid in 2 ml of trifluoroacetic acid. The benzoyl protective group is eliminated by the action of concentrated ammonia solution at 55° C. Purification is effected by RP-HPLC on C8 using an ascending gradient of TFA in acetonitrile. Yield: 28 mg (45%).

Example 44

Investigation of oligomer binding to single-stranded DNA using gel-shift analyses 1 μg of oligonucleotide of appropriate base sequence is labelled in a customary manner at the 5' end using polynucleotide kinase and γ-ATP in a volume of 10 μl (Sambrook, Fritsch, Maniatis: Molecular Cloning, A Laboratory Manual, Cold Spring Harbor, 1989). After the labelling, the sample is heated at 70° C. for 10 min. to denature the enzyme and is subsequently mixed with 9 μg of unlabelled oligomer. A desired quantity of nucleic acid-binding oligomer being tested (1–10 μg) is added to 1 μl of this mixture and the whole is incubated at 22° C. (room temperature) for 30 min. in a volume of 20 μl (hybridization). After that, the sample is placed on ice for 30 min. A labelled oligomer which is not hybridized is treated in the same way and serves as the control. The samples are loaded onto a 15% polyacrylamide gel using 1 x Tris-borate-EDTA buffer. The gel and the buffer were precooled in a refrigerator (8° C.) and the electrophoresis was left to run overnight at 55 V in a refrigerator. Following the electrophoresis, an autoradiogram was prepared on Agfa film (exposure times, 1–16 hours).

Exemplifying Experiment 45

Demonstration of strand displacement in double-stranded plasmid DNA by nucleic acid-binding oligomers The tests were carried out as follows:

(The plasmid DNA employed in the example is only a model substrate in the test. Other plasmids which contain polyadenine sequence regions at defined distances from each other can also be used).

Double-stranded, circular plasmid DNA, which is of 4880 base pairs in length and which contains two poly-adenine sequence regions having at least nine consecutive adenine nucleotides, which sequence regions are at a distance apart of 1150 base pairs, is used in the tests described here.

Six samples, set up in parallel and designated (1–6), each contained 1.0 μg of uncut plasmid DNA in 14 μl of $H_2O$. In each case, 1 μl volumes of solutions of 0.01 μg, 0.1 μg, 1.0 μg and 2.0 μg of nucleic acid-binding oligomers from Example 25 H—(III T)$_{12}$—Lys—OH were added to samples 3 to 6 and the mixtures were incubated in sealed Eppendorf reaction tubes at 37° C. for 45 min. Subsequently, 4 μl of buffer (250 mM Na acetate, 1 M NaCl, 2.5% glycerol, 5 mM $ZnCl_2$, pH 4.4) were added to all the samples while 1 μl of S1 nuclease from *Aspergillus oryzae* (from Boehringer Mannheim), having an activity of 10 U/μl, was added to each of samples 2 to 6. After having been incubated at 30° C. for 15 minutes, the samples were placed on ice, 1 μl of 0.5 M EDTA and 3 μl of loading buffer (50% glycerol, 0.25% bromophenol blue in 40 mM Tris/HCl, 20 mM sodium acetate, 1 mM EDTA, pH=7.2) were added, and, without delay, the samples were fractionated electrophoretically on 1.2% agarose gels and, after staining with ethidium bromides, the sizes of the resulting plasmid fragments on the gel were determined by comparison with a molecular weight standard (1-kb ladder, from Gibco-BRL, D-7514 Eggenstein) on a transilluminator using 254 nm UV light. It was found that DNA fragments of 4880 base pairs (plasmid linearization) and 3720 and 1150 base pairs (sequence-selective fragmentation) were visible in the samples containing a concentration of oligomers from Example 25 which was greater than 0.1 μg (samples 5 and 6).

Using a modified test mixture, in which, instead of the circular, uncut plasmid DNA, a plasmid DNA was added to the samples which was linearized by restriction endonuclease digestion in the immediate vicinity of one of the two poly-adenine sequence regions, the DNA fragments of 3730 and 1150 base pairs in length could likewise be demonstrated in samples 5 and 6.

Using this series of tests, it was possible to demonstrate the concentration-dependent and sequence-selective binding of the oligomer from Example 25 to double-stranded DNA and to demonstrate the single-stranded DNA, arising as a consequence, by means of S1 nuclease digestion at high salt concentrations (single-stranded specific activity of S1 nuclease).

Example 46

Inhibition of gene expression (in-vitro translation test)

A rabbit reticulocyte lysate from Promega, Madison, Wis. was used for the in-vitro translation, as were in-vitro transcribed mRNA of the tat gene from HIV-I and of the delta subunit of the acetylcholine receptor from Torpedo californica. Other genes can be used in the same way. The cDNA constructs of the genes were transcribed in a customary manner using SP6 RNA polymerase or T7-RNA polymerase (Sambrook et al., ditto), and the DNA plasmid was subsequently digested with DNase and the mRNA treated with phenol and precipitated three times with ethanol. 1–2 μg of the resulting mRNA were employed for the in-vitro translation in the presence of $^{35}$S-labelled cysteine. The radioactive protein which was formed was analysed on a 6–18% or 6–10% discontinuous SDS PAGE in accordance with Laemmli, U.K. (1970) Nature 227, 683–685.

In order to measure quantitatively the inhibition of translation by nucleic acid-binding oligomers, a desired quantity of oligomer (0.01–2 μg) was added to the mRNA and translation was then carried out in the rabbit reticulocyte lysate as described above. Autoradiographs of SDS polyacrylamide electrophoresis gels from the test mixtures were quantitatively evaluated using a scanner.

Example 47

Stability towards proteases

In order to investigate protease stability, using the nucleic acid-binding oligomers from Examples 24 and 25 in an exemplifying manner, mixtures of in each case 75 μg of oligomer, and containing 5 μl of protease, as listed in the table below, and 5 μl of protease buffer (1 M Tris/Hcl, pH 7.5; 0.4 M $CaCl_2$), were made up to a total volume of 50 μl with doubly distilled $H_2O$ and incubated at 37° C. for 3 hours.

Cell extracts from T lymphocytes and blood were also employed for the stability investigations in addition to the purified, defined proteases. For this purpose, 50 ml of cell suspension were centrifuged down at 2000 rpm, taken up in 500 μl of Tris/HCl buffer, pH 7.5; 40 mM $CaCl_2$, and lysed with 5 μl of 20% SDS. Following dialysis against 0.1 M Tris/HCl, pH 7.5; 40 mM $CaCl_2$, and a change of buffer after 4 hours, 5 μl were employed directly in the test. Blood was lysed directly with doubly distilled $H_2O$ and 5 μl were then employed in the test. Bovine serine albumin (BSA) and lysozyme were used as positive controls for digestion by the proteases.

An equal volume of protein loading buffer (8% β-mercaptoethanol, 3.5% SDS, 8 M urea, 125 mM Tris/HCl, pH 8; 0.02% bromophenol blue, 20% glycerol) was added to the mixtures.

30 μl volumes of the mixtures were then loaded onto a polyacrylamide gel (stacking gel, 4%, resolving gel, 15%), and electrophoresed at 280 V/40 mA for 2.5 hours.

Subsequently, the gel was analysed by UV shadowing. To do this, the gel was laid on a Merck TLC chromatoplate (silica gel 60 F 254) containing UV indicator, and evaluated at 254 nm. In addition to this, silver staining of the protein bands was carried out. To do this, the gel was incubated in the following solutions:

1. 50% methanol, 5% TCA, 30 minutes' incubation
2. 50% methanol, 5% TCA, 1% $CuCl_2$, $ZnCl_2$, 15 minutes
3. 10% ethanol, 5% acetic acid, 15 minutes
4. 0.01% $KMnO_4$, in water, 15 minutes
5. 10% ethanol, 5% acetic acid, 10 minutes
6. 10% ethanol, 15 minutes
7. $H_2O$, 15 minutes
8. 0.01% $AgNO_3$, 10 minutes
9. $H_2O$, 20 seconds
10. 10% $K_2CO_3$, 1 minute Developer (0.0075% formaldehyde, 10% $H_2CO_3$), 6–10 minutes 12. 5% acetic acid, 10% ethanol, 1 minute
13. $H_2O$, 2 hours The gels were either stored in 5% glycerol in plastic films or else treated in a gel dryer.

The results are presented in the table below. The nucleic acid-binding oligomers from Examples 24 and 25 are stable towards the proteases and cell extracts which were tested.

Stability towards proteases of nucleic acid-binding oligomers from Examples 24 and 25

| Protease | H-(IIIT)$_8$-Ala—OH | H-(IIIT)$_{12}$-Lys—OH |
|---|---|---|
| Proteinase K | + | + |
| Pronase E | + | + |
| Trypsin | + | + |
| Endoprotease LYS—C | + | + |
| V8 Protease (GLU—C) | + | + |
| Protease XXI | + | + |
| Protease IX | + | + |
| Extracts of: | | |
| T-lymphocyte cells (HUT, U 937) | + | + |
| Blood | + | + |

Example 48

Stability towards nucleases

In order to investigate the stability of the nucleic acid-binding oligomers from Examples 24 and 25 towards nucleases, mixtures of in each case 75 µg of oligomer together with 5 µl of nuclease (40 units), as listed in the table, and 5 µl of nuclease buffer (S1 nuclease buffer, 0.3 M potassium acetate, pH 4.6; 2.5 M NaCl, 10 mM ZnSO$_4$, 50% glycerol) were made up to a total volume of 50 µl with doubly distilled H$_2$O and incubated at 37° C. for 3 hours.

Cell extracts from T-lymphocytes and blood were also employed for the stability investigations in addition to the purified, defined nucleases. For this purpose, 50 ml of cell suspension were centrifuged down at 2000 rpm, taken up in 500 µl of Tris/HCl buffer, pH 7.5; 40 mM CaCl$_2$, and lysed with 5 µl of 20% SDS. Following dialysis against 0.1 M Tris/HCl, pH 7.5; 40 mM CaCl$_2$, and a change of buffer after 4 hours, 5 µl were employed directly in the test. Blood was employed directly following lysis with doubly distilled H$_2$O. A 25mer oligonucleotide diester was employed as the positive control for digestion by the nucleases.

An equal volume of protein loading buffer (8% β-mercaptoethanol, 3.5% SDS, 8=M urea, 125 mM Tris/HCl, pH 8; 0.02% bromophenol blue, 20% glycerol) was added to the mixtures.

30 µl volumes of the mixtures were then loaded onto a polyacrylamide gel (stacking gel, 4%, resolving gel, 15%), and electrophoresed at 280 V/40 mA for 2.5 hours.

Subsequently, the gel was analysed by UV shadowing. To do this, the gel was laid on a Merck TLC chromatoplate (silica gel 60 F 254) containing UV indicator, and evaluated at 254 nm. The results are presented in the table below. The oligomers are stable towards the nucleases and cell extracts which were tested. Stability towards nucleases of the nucleic acid-binding oligomers from Examples 24 and 25

| Nuclease | H-(IIIT)$_8$-Ala—OH | H-(IIIT)$_{12}$-Lys—OH |
|---|---|---|
| S1 nuclease | + | + |
| Bal31 nuclease | + | + |
| T-lymphocyte extract | + | + |
| Blood | + | + |

("+" denotes stability; no enzymic degradation)

We claim:

1. A compound of the formula I

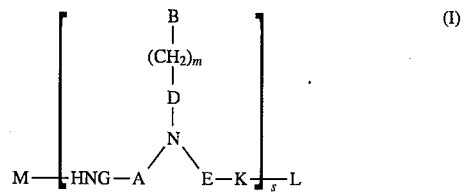

in which

A represents —(CH$_2$)$_n$- or —CO—,

B represents all natural or unnatural nucleobases, or derivatives derived therefrom by chemical modification, or halogenated precursors thereof, optionally substituted on the amino groups by protective groups selected from the group consisting of acetyl, trifluoroacetyl, trichloroacetyl, benzoyl, phenylacetyl, benzyloxycarbonyl, tertbutyloxycarbonyl, allyloxycarbonyl or (9-fluorenyl)methoxycarbonyl, or other protective groups which are customary in peptide and nucleic acid chemistry, or possessing free amino groups, D represents —(CO)$_p$—, E and G, independently of each other, represent —CHR—, where R represents H or a residue of a natural or unnatural amino acid selected from the group consisting of glycine, alanine, valine, leucine, isoleucine, serine, threonine, cysteine, methionine, phenylalanine, tyrosine, histidine, tryptophan, lysine, ornithine, asparagine, aspartic acid, glutamine, glutamic acid, arginine, proline, hydroxyproline or sarcosine, dehydroamino acids selected from the group consisting of dehydroalanine or dehydro-α-aminobutyric acid, phenylglycine, 4-nitrophenylalanine, 3-nitrophenylalanine, 2-nitrophenylalanine, 2-, 3- or 4-aminophenylalanine, 3,4-dichlorophenylalanine, 4-iodophenylalanine, 4-methoxyphenylalanine, 1-triazolylalanine, 2-pyridylalanine, 3-pyridylalanine, 4-pyridylalanine, 1-naphthylalanine or 2-naphthylalanine, optionally possessing protective groups, in their D or L form, or, optionally, E and G are linked together via an alkyl chain —(CH$_2$)$_q$—, K represents —CO—, —SO$_2$— or —CH$_2$—, L can be a carrier system, reporter ligand, a solubility-mediating group or hydrogen, M can, independently of L, be a carrier system, reporter ligand, a solubility-mediating group or hydrogen, m can be 0, 1, 2 or 3, n can be 0, 1, 2, 3 or 4, p can be 0, 1 or 2, q can be 0, 1 or 2, and s can assume values of between 1 and 30 containing the radical of a compound selected from the group consisting of
4-tert-butyloxycarbonylamino-N-[(thymin-1-yl)acetyl]-L-cis-proline,
N-[(N$^4$-benzoylcytosin-1-yl)acetyl]-4-tert-butyloxycarbonylamino-L-cis-proline,
4-tert-butyloxycarbonylamino-N-[(thymin-1-yl)-acetyl]-L-trans-proline,
4-tert-butyloxycarbonylamino-N-[(N$^6$-benzyloxycarbonyl-adenin-9-yl)acetyl]-L-cis-proline,
4-tert-butyloxycarbonylamino-N-[(N$^6$-benzyloxycarbonyl-adenin-9-yl)acetyl]-L-trans-proline, and 4-tert-butyloxycarbonylamino-N-[(N$^4$-benzyloxycarbonyl-cytosin-1-yl)acetyl]-L-trans-proline.

2. A compound of the formula I according to claim 1 in which

A represents —(CH$_2$)$_n$— or —CO—,

B represents all natural nucleobases or halogenated precursors thereof, optionally substituted on the amino groups by protective groups selected from the group consisting of acetyl, trifluoroacetyl, trichloroacetyl, benzoyl, phenylacetyl, benzyloxycarbonyl, tert-butyloxycarbonyl, allyloxycarbonyl or (9-fluorenyl) methoxycarbonyl, or other protective groups which are customary in peptide and nucleic acid chemistry, or possessing free amino groups, D represents —(CO)$_p$—, E and G, independently of each other, represent —CHR—, where R represents H or a residue of a natural or unnatural amino acid selected from the group consisting of glycine, alanine, valine, leucine, isoleucine, serine, threonine, cysteine, methionine, phenylalanine, tyrosine, histidine, tryptophan, lysine, ornithine, asparagine, aspartic acid, glutamine, glutamic acid, arginine, proline, hydroxyproline or sarcosine, dehydroamino acids selected from the group consisting of dehydroalanine or dehydro-α-aminobutyric acid, other unnatural amino acids selected from the group consisting of phenylglycine, 2-pyridylalanine, 3-pyridylalanine, 4-pyridylalanine, 1-naphthylalanine or 2-naphthylalanine, optionally possessing protective groups, in their D or L form, or, optionally, E and G are linked together via an alkyl chain —(CH$_2$)$_q$—, K can be —CO—, —SO$_2$— or —CH$_2$—, L can be a carrier system, reporter ligand, a solubility-mediating group or hydrogen, M can, independently of L, be a carrier system, reporter ligand, a solubility-mediating group or hydrogen, m can be 0, 1, 2 or 3, n can be 0, 1, 2 or 3, p can be 0 or 1, q can be 0, 1 or 2, and s can assume values of between 3 and 20.

3. A compound of the formula (I) according to claim 1 in which

A represents —(CH$_2$)$_n$— or —CO—,

B represents all natural nucleobases or halogenated precursors thereof, optionally substituted on the amino groups by protective groups selected from the group consisting of acetyl, trifluoroacetyl, trichloroacetyl, benzoyl, phenylacetyl, benzyloxycarbonyl, tert-butyloxycarbonyl, allyloxycarbonyl or (9-fluorenyl)methoxycarbonyl, or other protective groups which are customary in peptide and nucleic acid chemistry, or possessing free amino groups, D represents —(CO)$_p$—, E and G, independently of each other, represent —CHR—, where R represents H or a residue of a natural or unnatural amino acid selected from the group consisting of glycine, alanine, valine, leucine, isoleucine, serine, threonine, cysteine, methionine, phenylalanine, tyrosine, histidine, tryptophan, lysine, ornithine, asparagine, aspartic acid, glutamine, glutamic acid, arginine, proline, hydroxyproline, sarcosine, dehydroalanine or dehydro-α-aminobutyric acid, optionally possessing protective groups, in their D or L form, or, optionally, E and G are linked together via an alkyl chain —(CH$_2$)$_q$—, K is —CO—, L can be a carrier system, reporter ligand, a solubility-mediating group or hydrogen, M can, independently of L, be a carrier system, reporter ligand, a solubility-mediating group or hydrogen, m can be 0, 1 or 2, n can be 0, 1, 2 or 3, p can be 0 or 1, q can be 0 or 1, and s can assume values of between 3 and 18.

4. A compound according to claim 1, containing the radical of 4-tert-butyloxycarbonylamino-N-[(thymin-1-yl)acetyl]-L-cis-proline.

5. A compound according to claim 1, containing the radical of N-[(N$^4$-benzoylcytosin-1-yl)acetyl]-4-tert-butyloxycarbonylamino-L-cis-proline.

6. A compound according to claim 1, containing the radical of 4-tert-butyloxycarbonylamino-N-[(thymin-1-yl)-acetyl]-L-trans-proline.

7. A compound according to claim 1, containing the radical of 4-tert-butyloxycarbonylamino-N-[(N$^6$-benzyloxycarbonyl-adenin-9-yl)-acetyl]L-cis-proline.

8. A compound according to claim 1, containing the radical of 4-tert-butyloxycarbonylamino-N-[(N$^6$-benzyloxycarbonyl-adenin-9-yl)acetyl]-L-trans-proline.

9. A compound according to claim 1, containing the radical of 4-tert-butyloxycarbonylamino-N-[(N$^4$-benzyloxycarbonyl-cytosin-1-yl)-acetyl]-L-trans-proline.

10. A compound selected from the group consisting of 4-tert-butyloxycarbonylamino-N-[(thymin-1-yl)acetyl]-L-cis-proline, N-[(N$^4$-benzoylcytosin-1-yl)acetyl]-4-tert-butyloxycarbonylamino-L-cis-proline, 4-tert-butyloxycarbonylamino-N-[(thymin-1-yl)-acetyl]-L-trans-proline, 4-tert-butyloxycarbonylamino-N-[(N$^6$-benzyloxycarbonyl-adenin-9-yl)-acetyl]-L-cis-proline, 4-tert-butyloxycarbonylamino-N-[(N$^6$-benzyloxycarbonyl-adenin-9-yl)acetyl]-L-trans-proline, and 4-tert-butyloxycarbonylamino-N-[(N$^4$-benzyloxycarbonyl-cytosin-1-yl)-acetyl]-L-trans-proline.

11. A compound according to claim 10, wherein such compound is 4-tert-butyloxycarbonylamino-N-[(thymin-1-yl)acetyl]-L-cis-proline.

12. A compound according to claim 10, wherein such compound is N-[(N$^4$-benzoylcytosin-1-yl)acetyl]-4-tert-butyloxycarbonylamino-L-cis-proline.

13. A compound according to claim 10, wherein such compound is 4-tert-butyloxycarbonylamino-N-[(thymin-1-yl)-acetyl]-L-trans-proline.

14. A compound according to claim 10, wherein such compound is 4-tert-butyloxycarbonylamino-N-[( N$^6$-benzyloxycarbonyl-adenin-9-yl)-acetyl]L-cis-proline.

15. A compound according to claim 10, wherein such compound is 4-tert-butyloxycarbonylamino-N-[(N$^6$-benzyloxycarbonyl-adenin-9yl)acetyl]-L-trans-proline.

16. A compound according to claim 10, wherein such compound is 4-tert-butyloxycarbonylamino-N-[(N$^4$-benzyloxycarbonyl-cytosin-1-yl)-acetyl]-L-trans-proline.

* * * * *